United States Patent [19]
Mattson

[11] Patent Number: 4,779,621
[45] Date of Patent: Oct. 25, 1988

[54] XENON CALIBRATION PHANTOM

[75] Inventor: Rodney A. Mattson, Mentor, Ohio

[73] Assignee: Picker International, Inc., Highland Hts., Ohio

[21] Appl. No.: 16,266

[22] Filed: Feb. 19, 1987

[51] Int. Cl.$^4$ .............................................. A61B 6/00
[52] U.S. Cl. .................................. 128/654; 128/659; 378/18; 378/207
[58] Field of Search ............... 128/654, 659, 716, 719, 128/730, 653; 378/18, 207

[56] References Cited

U.S. PATENT DOCUMENTS

| | | | |
|---|---|---|---|
| 3,769,966 | 11/1973 | Youdin et al. | 128/654 |
| 4,233,507 | 11/1980 | Volz | 378/207 |
| 4,323,782 | 4/1982 | Riihimaki et al. | 378/207 |
| 4,527,057 | 7/1985 | Guyton et al. | 378/207 |
| 4,535,780 | 8/1985 | Gur et al. | 128/659 |
| 4,610,258 | 9/1986 | Colsher | 128/691 |
| 4,622,976 | 11/1986 | Timpe et al. | 128/654 |
| 4,663,772 | 5/1987 | Mattson et al. | 378/207 |

FOREIGN PATENT DOCUMENTS

| | | | |
|---|---|---|---|
| 2418786 | 4/1973 | Fed. Rep. of Germany | 128/654 |
| 2831513 | 1/1980 | Fed. Rep. of Germany | 378/207 |
| 3522113 | 1/1986 | Fed. Rep. of Germany | 128/659 |
| 0147229 | 5/1979 | Japan | 128/654 |

OTHER PUBLICATIONS

"Experimental Xenon Enhancement with CT Imaging: Cerebral Applications", B. P. Drayer et al., AJR:134, Jan. 1980, pp. 39-44.

"Local Cerebral Blood Flow by Xenon Enhanced CT", D. Gur et al., Stroke, vol. 13, No. 6, pp. 750-758, Nov.--Dec. 1982.

"Regional Cerebral Blood Flow Measurements Using Stable Xenon Enhanced Computer Tomography: A Theoretical and Experimental Evaluation", P. R. S. Kishore et al., J. of Computer Assisted Tomography, vol. 8, No. 4, pp. 619-630, Aug. 1984.

Primary Examiner—Ruth S. Smith
Attorney, Agent, or Firm—Fay, Sharpe, Beall, Fagan, Minnich & McKee

[57] ABSTRACT

A xenon concentration phantom (A) is mounted in a CT scanner (B). A xenon/oxygen breathing gas mixture from a breathing gas supply system is (C) circulated through an analysis chamber (12) of the phantom before a human scan is commenced. The CT scanner measures the amount of radiation absorption attributable to the gas in the analysis chamber, which absorption varies in proportion to the concentration of xenon gas. The measured radiation absorption is converted into a precise measurement or indication of the xenon concentration of the breathing gas. The precise xenon concentration measurement may be utilized to calibrate xenon gas detectors (80, 100) in the breathing gas supply system or to calibrate xenon concentration dependent diagnostic data generated during a subsequent patient scan while the patient is breathing the breathing gas.

19 Claims, 3 Drawing Sheets

XENON CALIBRATION PHANTOM

BACKGROUND OF THE INVENTION

The present invention relates to calibration methods and apparatus. It finds particular application in calibrating xenon gas concentrations used in conjunction with computed tomography scans or examinations and will be described with particular reference thereto. It is to be appreciated, however, that the invention may find application in the calibration of xenon and other gas concentrations in conjunction with gas imaging systems, other medical diagnostic scanners, or the like.

Heretofore, xenon enhanced computed tomography has been utilized for diagnostic examinations, particularly in the derivation local blood flow maps. Xenon gas is absorbed into the blood. Because xenon is a noble gas, it does not form stable compounds with other elements. In concentrations under 50%, it is generally considered medically safe when used as an inhalant, although it does have mild narcotic effects. In higher concentrations, the xenon can be toxic and in very high concentrations, it can lethal.

Because xenon is about 200 times more absorptive of x-radiation than air, it has been used in imaging techniques which developed images based on patterns of absorbed xenon. Typically, a mixture of 30% xenon and 30% oxygen was breathed by the patient undergoing CT examination. Oxygen and xenon concentration sensors automatically adjusted the flow of gas from separate oxygen and xenon sources in order to maintain the concentration of xenon in the breathed gases substantially constant. A base line scan of the patient was made before the patient started breathing xenon containing gas, conventionally with the patient breathing room air.

After the patient started breathing the xenon gas mixture, a series of scans of each body section was taken at selected time intervals. The series of scans recorded the absorption of the inhaled xenon from the blood into each body section of the body tissues. The rate of xenon build up or absorption in each section over the series of scans was determined. The concentration of xenon in the blood was determined by measuring the xenon concentration in the end tidal exhaled gases in the respiration cycle corresponding to each scan. The xenon-blood partition coefficient and the xenon blood flow were calculated for each section from the absorption rate and blood xenon concentration data collected over the series of scans.

One drawback of these prior art techniques resided in the calibration of xenon concentrations. First, if the measurement of the xenon concentration in the breathing gas were grossly miscalibrated, the patient could breath an injuriously high concentration of xenon. Second, any inaccuracy in the end tidal exhalation measurements caused corresponding errors in the calculated partition coefficient $\lambda$ and flow maps.

The present invention provides an unambiguous technique which utilizes x-ray absorption to calibrate the xenon gas mixture delivery system and to confirm that safe concentrations of xenon will be delivered to the patient.

SUMMARY OF THE INVENTION

In accordance with one aspect of the present invention, a calibration phantom is provided for medical CT scanners. A gas analysis chamber is operatively connected with an inlet means for receiving gas to be analyzed and with an outlet means for discharging the gas. In this manner, the gas flows from the inlet through the analysis chamber and out the outlet means. A scanner mounting means selectively mounts at least the analysis chamber in an image region of a medical diagnostic scanner.

In accordance with another aspect of the present invention, a gas concentration calibration system is provided. A CT scanner selectively radiates a generally planar image region with penetrating radiation. A breathing gas supply system supplies breathing gas which has substantially a preselected concentration of xenon gas. A radiation translucent analysis chamber of a phantom is selectively disposable in the image region. The analysis chamber is operatively connected with the breathing gas supply system such that at least a portion of the supplied breathing gas flows through the measurement chamber.

In accordance with yet another aspect of the present invention, a xenon gas calibration method is provided. A flow of breathing gas which contains generally a preselected concentration of xenon gas is provided. At least a portion of the breathing gas is caused to flow through a phantom disposed in an image region of a CT or other radiographic scanner. The phantom is irradiated by a beam of radiation which has a preselected amount of power. The attenuation of the radiation beam attributable to radiation absorption by the breathing air is measured. The measured attenuation varies in accordance with the concentration of xenon gas in the phantom. The measured radiation attenuation is converted into an indication of the concentration of xenon in the breathing gas. In this manner, a precise measurement of the concentration of xenon in the breathing gas is provided.

A first advantage of the present invention is that it provides a more precise and accurate measurement of the concentration of xenon in a breathing gas.

Another advantage of the present invention is that it improves safety by confirming that medically safe concentrations of xenon will be provided in the breathing gas.

Another advantage of the present invention is that it provides for more accurate and meaningful medical and diagnostic data.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
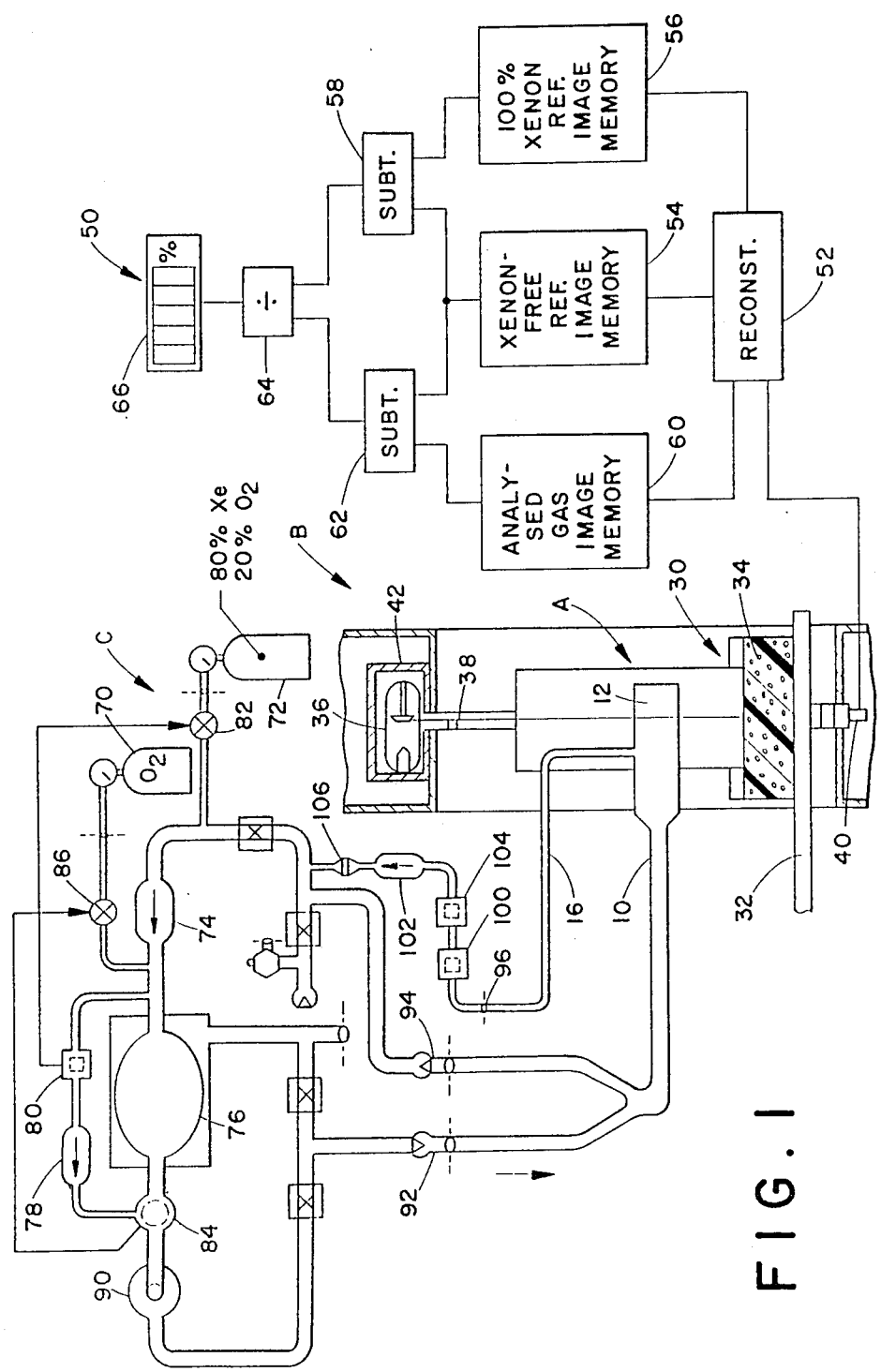
FIG. 1 is diagrammatic illustration of a xenon gas calibration phantom in accordance with the present invention in combination with a CT scanner and a closed or recirculation breathing gas supply means.

With reference to FIG. 1, a gas calibration phantom A is selectively positionable in a diagnostic apparatus B, such as a CT scanner. The phantom is in fluid connection with a gas supply means C for supplying a xenon and oxygen breathing gas mixture. After the gas supply means is disconnected from the phantom it is connected wtih a breathing mask. The phantom is removed from the scanner and scans of the patient are conducted.

Figures 2, 3:
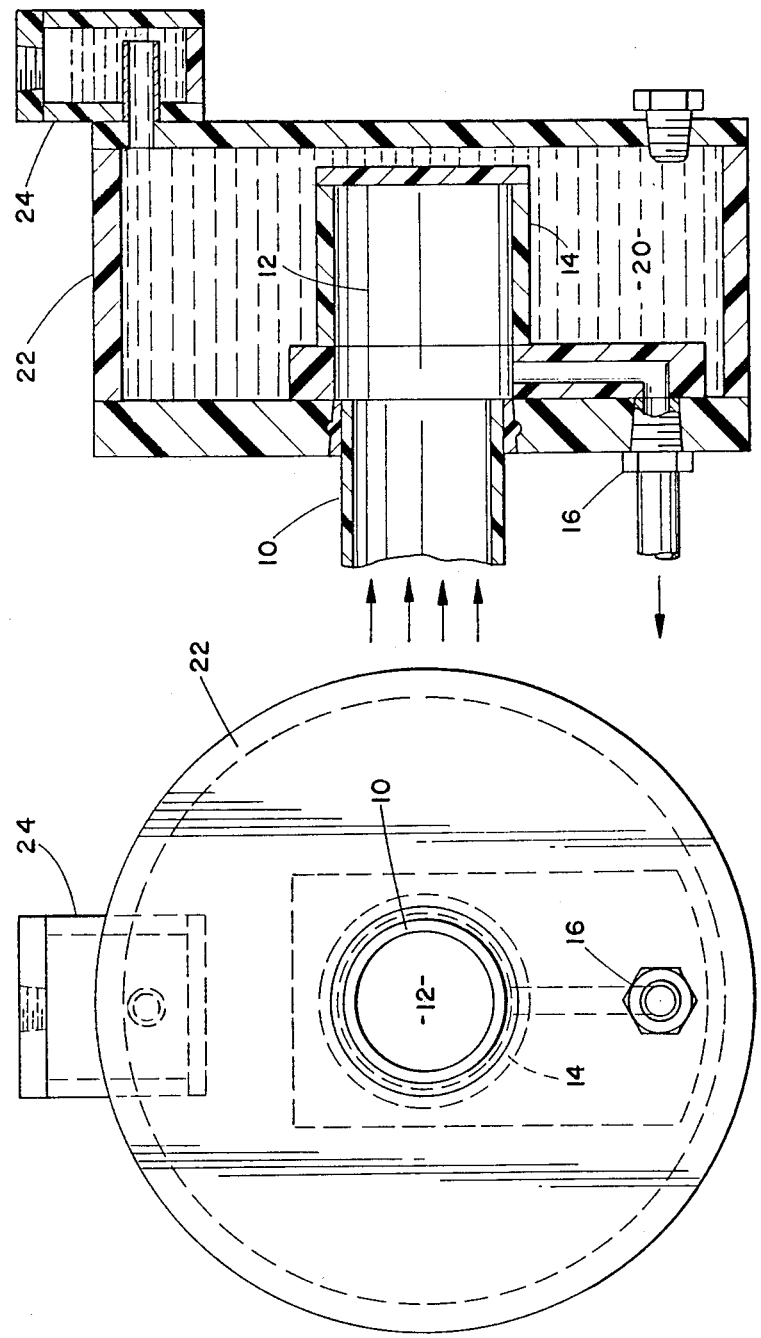
FIG. 2 is a detailed side sectional view of a preferred embodiment of the phantom.
FIG. 3 is a front plan view of the phantom of FIG. 2.

With continuing reference to FIG. 1 and further reference to FIGS. 2 and 3, the phantom A has an inlet means 10 which receives the breathing gas that would have gone to a patient or other gas to be analyzed and supplies it to an analysis chamber 12. The analysis chamber is defined by a sidewall, preferably a cylinder 14, of a radiation translucent material such as plastic. The analysis chamber is interconnected with an outlet means 16. In this manner, the gas to be analyzed can flow through the analysis chamber to establish an equilibrium condition therein. The inlet means 10 is selectively detachable from the analysis chamber 12 such that a vial containing a reference concentration of xenon can be inserted into the analysis chamber. One hundred percent xenon has been found to be convenient although other concentrations may be selected.

The analysis chamber 12 adjoins a reference material 20 such as water or plastic. In the preferred embodiment, the reference material is disposed in a cylindrical, annular ring surrounding the analysis chamber 12. In the illustrated embodiment in which the reference material is water, an annular reference material reservoir 22 is constructed of the radiation translucent material. A level control means 24 assures that the reference material reservoir is maintained completely filled with water with no air space at the top.

Preferably, the diameter of the analysis cylinder is greater than one inch to minimize the effects of off-focal radiation and spectral artifacts. The reference material is selected such that the annular ring of the reference material absorbs some but not a great number of x-ray photons to assure a low noise scan with moderate x-ray power levels. A water or plastic phantom with a four to six inch diameter is preferred.

With reference again to FIG. 1, a phantom mounting means 30 is provided for positioning or mounting the phantom in an image region of the CT scanner B. In the preferred embodiment, the phantom mounting means includes a patient support table 32 of the CT scanner and a patient head support 34 which is disposed on the patient support table. The CT scanner includes a source 36 of penetrating radiation which irradiates the generally planar imaging region with a generally planar beam 38 of radiation. An array of x-ray detectors 40 is disposed opposite the phantom from the x-ray source and in line with the image region to receive the radiation which has traversed the phantom. The x-ray source 36 is mounted in a rotatable housing 42 such that the beam of radiation can be rotated peripherally around the phantom and the image region. The array of detectors 40 may either rotate with the radiation beam or may completely surround the image region.

From the absorption of radiation, the concentration of a selected gaseous component, particularly xenon in the analysis chamber is determined. With a 60 KEV x-ray beam, the mass absorption coefficient of xenon is 7.80 $cm^2/gm$; whereas the mass absorption coefficient for oxygen is 0.189 $cm^2/gm$. In addition to having a much higher mass absorption coefficient, the density of xenon is much higher than air, i.e. xenon has a density of 0.005896 $gm/cm^3$ and air has a density of 0.001205 $gm/cm^3$. The linear absorption coefficient is the product of the mass absorption coefficient and the density of the gas. That is, the linear absorption coefficient for xenon is 0.046 $cm^{-1}$ and for air is 0.000228 $cm^{-1}$. Thus, xenon absorbs approximately 200 times more 60 KEV x-radiation per unit length as does air. By comparing the amount of radiation absorbed by gas having an unknown quantity of xenon in the analysis chamber with the absorption when the chamber contains a known xenon concentration, the concentration of xenon of the unknown gas in the analysis chamber can be precisely determined.

By way of example, for a 60 KEV x-ray beam with a 6 inch diameter water reference material surrounding the analysis chamber, the CT number within the analysis chamber will rise by 223 Hounsfield units when xenon-free air is replaced by 100% xenon. When the gas concentration is 50% xenon and 50% oxygen, the CT number in the analysis region is 112 Hounsfield units higher than air. Analogously, a 25% concentration produces a net change of 56 Hounsfield units. Due to this linear relationship in the change of the Hounsfield units with percent of xenon, the concentration of xenon within the analysis chamber can be readily determined.

A xenon concentration determining means 50 is interconnected with the radiation detectors for determining the concentration of xenon in the analysis chamber. A conventional CT scanner reconstruction means 52 generates a first reference CT image with a first known xenon concentration in the analysis chamber. Preferably, the first known xenon concentration is zero, i.e. an image with xenon-free gas. The first reference image is stored in a first or xenon-free reference image memory means 54. A second reference image is generated with a second known xenon concentration, preferably 100% xenon gas in a vial inserted in the analysis chamber. The second reference image is stored in a second or 100% xenon reference image memory means 56. A difference means 58 determines the difference in the radiation absorption between the 100% xenon and the xenon-free image portions.

By way of example, with a 60% KEV x-ray source, xenon-free air might typically evidence a radiation absorption of $-998$ Hounsfield units and 100% xenon concentration might evidence an absorption of $-775$ Hounsfield units. The difference, i.e. $-775-(-998)=223$, is the 0-100% or full range difference. With a 50 KEV x-radiation source, the 0 to 100% full range difference would be 330 and with an 80 KEV x-ray source, the full range difference would be 115.

To analyse breathing gas with an unknown xenon concentration, the breathing gas is circulated through the analysis chamber until an equilibrium is reached. A third scan is conducted and the reconstruction means generates an analysed gas or unknown xenon concentration image which is stored in an analysed gas image memory means 60. A comparison means 62 compares the Hounsfield units for the xenon free and the unknown xenon concentration gas. More specifically, the comparison means subtracts the Hounsfield number of the xenon-free air from the Hounsfield number for the unkown xenon concentration gas. A xenon concentration determining means 64 determines a ratio of the unknown and xenon-free gas difference from the comparing means 62 to the 0 to 100% full range difference from the difference means 58. This ratio is displayed on a xenon concentration indicating means 66 to show the xenon concentration.

Continuing the foregoing example, the Hounsfield number for an unknown xenon concentration gas might be −948. The comparing means 62 subtracts the xenon-free gas Hounsfield number from the unknown xenon concentration Hounsfield number, i.e. −948−(−998)=50. The xenon concentration determining means 64 divides the two differences, i.e. 50÷223=0.224 or 22.4%. The 22.4% xenon concentratioon is displayed on the indicating means 66.

The breathing gas supply means C includes an oxygen supply 70 and a xenon supply 72. The xenon supply provides a mixture of 80% xenon and 20% oxygen to guarantee that the patient receives at least 20% oxygen even during a malfunction. A first blower 74 supplies xenon, oxygen, and recirculated gas for mixture with the oxygen. Most of the mixture passes to a breathing bag 76, but a fraction is conveyed by a pump 78 through a xenon detector 80. The xenon detector 80 determines the concentration of xenon in the gaseous mixture and controls a xenon control valve 82 to maintain the xenon concentration substantially constant. Typically, the xenon concentration is selected to be 30%. An oxygen probe 84 measures the concentration of oxygen in the breathing gas and controls an oxygen supply valve 86 to maintain the oxygen substantially constant. Typically, the oxygen is maintained constant at 30%.

A carbon dioxide absorber 90 absorbs carbon dioxide from the breathing gas which is supplied through a patient port outlet check valve 92 to a patient's breathing mask as the patient inhales. A patient port return check valve 94 returns the breathed gas to the system as the patient exhales. However, when a calibration of the xenon concentration is to be performed, the oxygen concentration phantom inlet means 10 is interconnected with the patient port check valves 92 and 94. The breathing gas then passes through the analysis chamber 12 and the outlet means 16 to a sample port 96. The sample port 96 is connected with the patient exhale return line to receive the xenon for detection as the patient exhales. The concentration of xenon at the end tidal portion of a patient's exhale cycle is linearly related to the concentration of xenon in the blood. A xenon detector 100 detects the xenon concentration of the exhaled gas.

Preferably, the xenon detectors 80 and 100 are calibrated from the unambiguous xenon concentration measurement made in conjunction with the phantom. In this manner, the medical diagnostic xenon concentration information from detector 100 is rendered more accurate by calibration with the xenon calibration phantom A.

A pump 102 pumps the returned gas through the xenon detector 100, a carbon dioxide detector 104, and a bacteria filter 106. Thereafter, the gas is returned to the breathing gas supply system to be recycled by the blower 74. After the calibration procedure, the patient and sample ports 92, 94, and 96 are connected with a breathing mask and conventional xenon inhalation images are taken of the patient.

Figure 4:
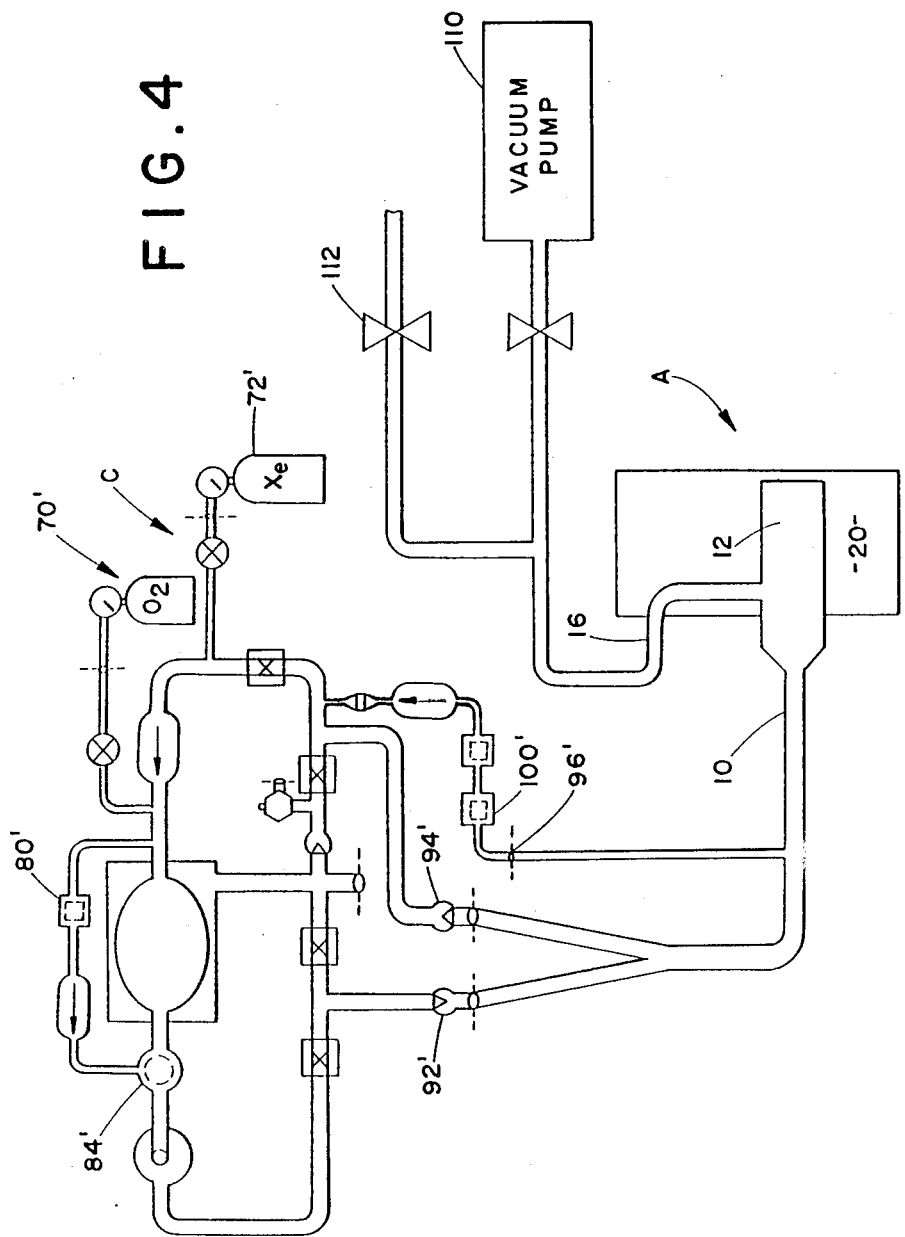
FIG. 4 is a diagrammatic illustration of a phantom in accordance with the present invention in combination with an open or non-recirculating breath gas supply system.

FIG. 4 illustrates the phantom A in combination with an open rather than closed gas supply system C. In the embodiment of FIG. 4, like elements with the embodiment of FIG. 1 are denoted by the same reference numeral but followed by a prime ('). A oxygen supply means 70' and a xenon supply means 72' under control of a xenon detector 80' and an oxygen probe 84' supply a xenon/oxygen mixture with a preselected xenon concentration. The phantom inlet 10 is connected with patient port check valves 92' and 94' as well as with a sample port 96'. A xenon detector 100' is connected with the sample port for detecting xenon concentration at the end of the patient's exhale cycle. The phantom outlet 16 is connected with a vacuum pump 110 which draws the xenon/oxygen mixture through the analysis chamber until an equilibrium concentration of gas is attained. The xenon CT scan is then conducted. Optionally, an alternate gas may be supplied through an alternate gas valve 112 and the phantom outlet 16.

The invention has been described with reference to the preferred embodiment. Obviously, modifications and alterations will occur to others upon reading and understanding the preceding detailed description. It is intended that the invention include all such alterations an modifications insofar as they come within the scope of the appended claims and the equivalents thereof.

Having thus described the preferred embodiment, the invention is now claimed to be:

1. A gas concentration calibration system comprising:
   (a) a means for irradiating an image region with penetrating radiation;
   (b) a breathing gas supply means for supplying breathing gas which has substantially a preselected concentration of xenon gas;
   (c) a phantom having a radiation translucent analysis chamber which is selectively disposed in the image region, the analysis chamber being connected with the breathing gas supply system such that at least a portion of the supplied breathing gas flows through the analysis chamber;
   (d) a radiation detecting means for detecting the penetrating radiation which has traversed the image region;
   (e) image reconstruction means for reconstructing an image from detected radiation, the image reconstruction means being connected with the radiation detecting means, the image including a measurement of radiation absorption in a region of the image corresponding to the analysis chamber; and
   (f) a xenon concentration means for determining the concentration of xenon gas in the analysis chamber from the radiation absorption measurement.

2. The system as set forth in claim 1 and further including an annular ring of a reference material surrounding the analysis chamber.

3. The system as set forth in claim 1 wherein the phantom includes an annular fluid tight chamber around the analysis chamber, the annular fluid tight chamber being filled with a liquid reference material.

4. The system as set forth in claim 3 wherein the reference material is water.

5. The system as set forth in claim 1 wherein the breathing gas supply means includes an oxygen supply, a xenon gas supply and a breathing gas analysis means for determining the relative concentration of oxygen and xenon gas in the breathing gas and for controlling at least one of the oxygen and xenon gas supply means for maintaining the relative concentration substantially constant.

6. A gas concentration calibration system comprising: an oxygen supply means for supplying oxygen;

a xenon supply means for supplying xenon;

a mixing means connected with the oxygen and xenon supply means for mixing the supplied oxygen and xenon to form a breathing gas;

a concentration determining means for less accurately determining a relative concentration of oxygen and xenon in the breathing gas;

a control means for controlling at least one of the oxygen and xenon gas supply means in accordance with the less accurately determined relative concentration for maintaining the relative concentration substantially constant, the control means being connected with the less accurate concentration determining means and at least one of the oxygen and xenon supply means;

a phantom having a radiation translucent chamber, the chamber connected with the mixing means such that at least a portion of the breathing gas flows through the chamber;

a means for irradiating the chamber with penetrating radiation;

a means for measuring radiation absorption by the breathing gas in the chamber; and, a means for more accurately determining the concentration of xenon in the breathing gas from the measured absorption, the more accurate concentration determining means being connected wtih the radiation absorption measuring means.

7. A calibration phantom for a medical diagnostic scanner, the phantom comprising:

an inlet means for receiving a gas to be analyzed;

an analysis chamber connected with the inlet means for receiving gas therefrom;

an outlet means for discharging gas, the outlet means being connected with the analysis chamber for discharging gas therefrom, whereby gas flows from the inlet means through the analysis chamber, and out the outlet means; and, a positioning means for selectively positioning the analysis chamber in an image region of the medical diagnostic scanner.

8. The phantom as set forth in claim 7 further including an annular ring of reference material surrounding the analysis chamber.

9. The phantom as set forth in claim 7 further including an annular fluid holding reservoir disposed annularly around the analysis chamber for receiving a reference liquid therein.

10. The phantom as set forth in claim 7 wherein the analysis chamber has a circular cross section which is at least 1.0 inches in diameter to minimize effects of off-focal radiation and beam hardening.

11. The phantom as set forth in claim 10 further including an annular ring with a nominal six inch outer diameter of a reference material.

12. The phantom as set forth in claim 7 wherein the positioning means includes a patient head support.

13. The phantom as set forth in claim 7 further including a means for measuring radiation absorption by the gas in the analysis chamber and means for deriving a concentration of a preselected gaseous component from the measured radiation absorption.

14. A method of xenon gas calibration comprising:

providing a flow of breathing gas which contains generally a preselected fraction of xenon gas;

causing at least a portion of the breathing gas to flow through a phantom disposed in a generally planar image region of a scanner;

irradiating the phantom with a beam of penetrating radiation having a preselected power;

measuring attenuation of the radiation beam attributable to radiation absorption by the breathing gas, the measured attentuation varying with the concentration of xenon gas in the phantom;

converting the measured radiation attenuation into an indication of the concentration of xenon in the breathing gas.

15. The method as set forth in claim 14 wherein the phantom includes an analysis chamber through which the breathing gas flows through and further including prior to the irradiating step surrounding the analysis chamber with a reference material.

16. The method as set forth in claim 14 further including:

disposing a reference gas with a known xenon concentration in the phantom;

irradiating the phantom containing the reference gas with the beam of radiation;

measuring the attenuation of the radiation beam attributable to the reference gas;

determining a difference in radiation attentuation between the breathing gas and the reference gas, and wherein the converting step includes converting the difference in the measured reference and breathing gas radiation attentuations into the indication of the xenon concentration.

17. The method as set forth in claim 14 wherein:

the irradiating step includes rotating a source of the penetrating radiation around the image region;

the measuring step includes detecting radiation from the source which has traversed the image region, reconstructing an image representation from the detected radiation, and determining the radiation attenuation from a section of the image corresponding to the breathing gas in the phantom.

18. The method as set forth in claim 14 wherein the breathing gas flow providing step includes supplying xenon and oxygen, mixing the xenon and oxygen to form the breathing gas, analysing the relative concentrations of xenon and oxygen in the breathing gas, and controlling the supply of at least one of the oxygen and xenon in accordance with the measured relative concentration, whereby the breathing gas has substantially the preselected relative concentration of oxygen and xenon.

19. A method of xenon gas calibration comprising:

supplying oxygen and xenon;

mixing the oxygen and xenon to form a oxygen/xenon mixture;

measuring the relative concentrations of oxygen and xenon in the oxygen/xenon mixture, which measured relative concentration may be inaccurate;

supplying the oxygen/xenon mixture in accordance with the measured relative concentration;

causing at least a portion of the oxygen/xenon mixture to flow through a phantom disposed in an image region;

irradiating the phantom with the beam of penetrating radiation having a preselected power;

measuring attenuation of the radiation beam attributable to radiation absorption of the oxygen/xenon mixture, the measured attenuation varying accurately with the concentration of xenon gas in the phantom;

converting the measured radiation attenuation into an indication of the concentration of xenon in the oxygen/xenon mixture, which indication of xenon concentration from the measured radiation attenuation is more accurate than the measured relative concentration; and, adjusting at least one of (1) the measured relative concentration and (2) a relative supply of oxygen and xenon in accordance with the xenon concentration indication determined from the radiation attenuation.

* * * * *